United States Patent [19]

Chen et al.

[11] 4,415,468
[45] Nov. 15, 1983

[54] DEODORIZATION OF N-VINYL MONOMERS

[75] Inventors: Albert C. Chen, East Brunswick; Frank A. Nagy, Edison, both of N.J.

[73] Assignee: Mobil Oil Corporation, New York, N.Y.

[21] Appl. No.: 260,572

[22] Filed: May 5, 1981

[51] Int. Cl.³ .............................................. A61L 9/01
[52] U.S. Cl. ...................................... 252/182; 422/5
[58] Field of Search ................ 252/182, 389 A; 422/5

[56] References Cited

U.S. PATENT DOCUMENTS 3,446,893 5/1969 Hanford et al. ................ 252/157 X
4,213,934 7/1980 Bellos et al. ................ 252/389 A X
4,231,894 11/1980 Lavin et al. ..................... 252/389 A

OTHER PUBLICATIONS

Encyclopedia of Chemical Technology, 2nd Ed. Kirk-Othmer, vol. 19, pp. 413–419.
The Random House Dictionary of the English Language, Jess Stein (1973), p. 574.

*Primary Examiner*—Howard E. Schain
*Attorney, Agent, or Firm*—A. J. McKillop; J. F. Powers, Jr.; E. F. Kenehan, Jr.

[57] ABSTRACT

This invention provides deodorized compositions and methods for preparing deodorized compositions comprising at least one odoriferous N-vinyl monomer (e.g., N-vinyl-2-pyrrolidone), and a sufficient deodorizing amount of an alkali metal bisulfite (e.g., $NaHSO_3$).

10 Claims, No Drawings

DEODORIZATION OF N-VINYL MONOMERS

BACKGROUND OF THE INVENTION

Various N-vinyl monomers such as N-vinyl-2-pyrrolidone (NVP) have an unpleasant odor. The unpleasant odor of NVP has been a particular problem since its introduction as a monomer into the radiation cure coatings (RC) market. In such coating techniques the monomer must be spread over a relatively large area, and the unpleasant odor associated with NVP cannot be contained.

SUMMARY OF THE INVENTION

This invention provides deodorized compositions comprising at least one odoriferous N-vinyl monomer and a sufficient deodorizing amount of an alkali metal bisulfite (especially $NaHSO_3$).

The invention further provides a method for deodorizing an odoriferous N-vinyl monomer comprising incorporating into the monomer a sufficient deodorizing amount of an alkali metal bisulfite (especially $NaHSO_3$).

Particular odoriferous N-vinyl monomers include N-vinyl caprolactam, N-vinyl carbazole and, especially, N-vinyl-2-pyrrolidone. When N-vinyl-2-pyrrolidone is deodorized in accordance with the present invention, preferred deodorizing amounts of $NaHSO_3$ are from about 0.05% to about 2% by weight, especially from about 1% by weight to about 2% by weight, based upon the weight of N-vinyl pyrrolidone, particularly depending upon the manner in which the sodium bisulfite is incorporated into the N-vinyl pyrrolidone and the desired degree of deodorization.

Preferably, the $NaHSO_3$ is incorporated into the odoriferous N-vinyl monomer by admixture and heating for a sufficient time and temperature to accomplish the desired degree of deodorization. Preferably, the $NaHSO_3$ is substantially dissolved in the deodorized composition.

The alkali metal bisulfite may be mixed with an N-vinyl monomer, per se, or with a composition comprising an N-vinyl monomer and other ingredients. For example, $NaHSO_3$ may be incorporated into a radiation curable coating composition comprising about 10–15% by weight of N-vinyl-2-pyrrolidone and the remainder being essentially a pigment such as $TiO_2$ and copolymerizable monomer such as one or more acrylic monomers.

EXAMPLE 1

Four samples of commercially available NVP monomer (V-Pyrol, a tradename of GAF, radiation cure grade) were prepared in the lab to evaluate odor reduction by addition of sodium bisulfite. The lab preparations contained 2% $NaHSO_3$, 1% $NaHSO_3$, 0.2% $NaHSO_3$ and 0.05% $NaHSO_3$ by weight. Approximately 100 g of NVP were weighed into suitable containers (120 g brown glass bottles) and the $NaHSO_3$ added. The samples were then placed into a hot water (about 60° C.) bath and stirred closed for about four hours. The heat was turned off and the samples were allowed to cool to room temperature while stirring.

The four samples of $NVP/NaHSO_3$ were rated for odor when they had reached room temperature, versus a control (0.0% $NaHSO_3$). The 2% and 1% $NaHSO_3$ samples were rated as having essentially no odor, and the 0.2% and 0.05% were rated as "improved" but still detectable odor. The samples were then aged over the weekend (about 60 hours) and rerated for odor versus the control. At this time, all detectable unpleasant odor had disappeared from the NVP samples containing the $NaHSO_3$. These samples were subsequently aged about 20 days at room temperature with no side effect (gels, etc.) and the unpleasant odor was not detectable.

EXAMPLE 2

A sample of a coating composition was also prepared to contain 0.1% by weight $NaHSO_3$ (1.0% of the NVP). The sample was prepared in a similar fashion to that set forth in Example 1, e.g., about four hours of heat and stir at 60° C., followed by cooling to room temperature. The strong, unpleasant odor associated with the NVP was no longer detectable in the cooled sample. Curing of the sample was then induced by an electon beam. Cure rate, completeness of cure and the physical properties of the cured coating, including E-beam cure response were not altered.

The present invention may comprise, consist essentially of or consist of the elements or method steps recited herein.

What is claimed is:

1. A deodorized composition at least one odoriferous N-vinyl monomer and a sufficient deodorizing amount of an alkali metal bisulfite.

2. A composition according to claim 1 wherein said odoriferous N-vinyl monomers are selected from the group consisting of N-vinyl-2-pyrrolidone, N-vinyl caprolactam and N-vinyl carbazole.

3. A composition according to claim 2, wherein said alkali metal bisulfite is $NaHSO_3$.

4. A composition according to claim 3, wherein said odoriferous N-vinyl monomer is N-vinyl-2-pyrrolidone.

5. A method for deodorizing an odoriferous N-vinyl monomer comprising incorporating into said monomer a sufficient deodorizing amount of an alkali metal bisulfite.

6. A method according to claim 5, wherein said odoriferous N-vinyl monomer is selected from the group consisting of N-vinyl-2-pyrrolidone, N-vinyl caprolactam and N-vinyl carbazole.

7. A method according to claim 6 wherein said alkali metal bisulfite is $NaHSO_3$.

8. A method according to claim 7, wherein said odoriferous N-vinyl monomer is N-vinyl-2-pyrrolidone.

9. A method accoring to claim 8, wherein said incorporation comprises the following steps:
   (i) mixing N-vinyl-2-pyrrolidone with from about 0.05% to about 2% by weight $NaHSO_3$, based upon the weight of N-vinyl-2-pyrrolidone;
   (ii) heating said mixture of step (i) with stirring for about 4 hours; and
   (iii) cooling said mixture of step (ii) to room temperature while stirring.

10. A method according to claim 9 wherein said step (i) comprises mixing N-vinyl-2-pyrrolidone with from about 1% to about 2% by weight $NaHSO_3$, based upon the weight of N-vinyl-2-pyrrolidone.

* * * * *

UNITED STATES PATENT AND TRADEMARK OFFICE
CERTIFICATE OF CORRECTION

PATENT NO. : 4,415,468
DATED : November 15, 1983
INVENTOR(S) : Albert C. Chen and Frank H. Nagy It is certified that error appears in the above–identified patent and that said Letters Patent are hereby corrected as shown below:

Col. 2, line 28 (Claim 1, line 1), insert --comprising-- between "composition" and "at".

Signed and Sealed this

Fourth Day of September 1984

[SEAL]

Attest:

GERALD J. MOSSINGHOFF

Attesting Officer      Commissioner of Patents and Trademarks